(12) United States Patent
Rollins, Sr.

(10) Patent No.: US 10,064,994 B2
(45) Date of Patent: Sep. 4, 2018

(54) AUTOMATIC INSULIN DELIVERY SYSTEM

(71) Applicant: IOWA STATE UNIVERSITY RESEARCH FOUNDATION, INC., Ames, IA (US)

(72) Inventor: Derrick K. Rollins, Sr., Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 183 days.

(21) Appl. No.: 15/137,519

(22) Filed: Apr. 25, 2016

(65) Prior Publication Data

US 2016/0339177 A1 Nov. 24, 2016

Related U.S. Application Data

(60) Provisional application No. 62/165,283, filed on May 22, 2015.

(51) Int. Cl.
| | | |
|---|---|---|
| *A61M 5/172* | (2006.01) | |
| *A61K 38/28* | (2006.01) | |
| *G06F 19/00* | (2018.01) | |

(52) U.S. Cl.
CPC ........... *A61M 5/1723* (2013.01); *A61K 38/28* (2013.01); *G06F 19/3468* (2013.01); *A61M 2205/3303* (2013.01); *A61M 2205/3576* (2013.01); *A61M 2205/50* (2013.01)

(58) Field of Classification Search
CPC ........ A61M 5/1723; A61M 2205/3303; A61M 2205/3576; A61M 2205/50; A61K 38/28; G06F 19/3468

USPC .............. 604/504–507, 65–67, 131, 151; 128/DIG. 12, 13

See application file for complete search history.

(56) References Cited

U.S. PATENT DOCUMENTS

| | | |
|---|---|---|
| 6,544,212 B2 | 4/2003 | Galley et al. |
| 8,273,052 B2 | 9/2012 | Damiano et al. |

(Continued)

OTHER PUBLICATIONS

Doyle, Frank, et al., "Glucose Control Strategies for Treating Type 1 Diabetes Mellitus", Journal of Process Control, 17, (2007), pp. 572-576.

(Continued)

*Primary Examiner* — Manuel Mendez
(74) *Attorney, Agent, or Firm* — McKee, Voorhees & Sease, PLC

(57) ABSTRACT

A system and method for automatically administering insulin based on a feedforward control. The automatic insulin delivery system may include a computing device comprising a processor, machine readable non-transitory media which stores the coupled-model of the invention, and a monitoring system. The machine readable transitory media may be configured to receive one or more inputs and the coupled-model may utilize a feedforward control to parameterize the inputs and generate an output that can be translated to a type and amount of insulin to be administered by the system. The input(s) received by the machine readable non-transitory media may be created by a user or received from one or more sensors. The method may include providing a model that is stored on a machine readable non-transitory media and administering insulin based on the output provided by the model.

20 Claims, 10 Drawing Sheets

(56) References Cited

U.S. PATENT DOCUMENTS

2010/0262117 A1 10/2010 Magni et al.
2014/0066886 A1* 3/2014 Roy .................. A61B 5/14532
604/504

OTHER PUBLICATIONS

Rollins, Derrick K., Sr., et al., "Dynamic Modeling with Correlated Inputs: Theory, Method, and Experimental Demonstration", Industrial & Engineering Chemistry Research, (2015), DOI: 10.1021, 9 pages.
Rollins, Derrick, "Use of Input-based Models for Improved Glucose Control in Type 1 Diabetes", Sep. 1, 2010-Aug. 31, 2012, Lay Abstract, 2 pages.
Kotz, Kaylee, et al., "Multiple-Input Subject-Specific Modeling of Plasma Glucose Concentration for Feedforward Control", Industrial & Engineering Chemistry Research, (2014), vol. 53, pp. 18216-18225.
Rollins, Derrick, K., et al., "Free-living inferential modeling of blood glucose level using only noninvasive inputs", Journal of Process Control, 20, (2010), pp. 95-107.
Rollins, Derrick, K., et al., "The Development of a Virtual Sensor in Glucose Monitoring for Non-Insulin Dependent People", Bioinformatics and Diabetes, vol. 1, Issue 1, 18 pages.

* cited by examiner

AUTOMATIC INSULIN DELIVERY SYSTEM

CROSS-REFERENCE TO RELATED APPLICATIONS

This application claims priority under 35 U.S.C. § 119 to provisional application Ser. No. 62/165,283, filed May 22, 2015, herein incorporated by reference in its entirety.

TECHNICAL FIELD

This invention relates generally to an automatic insulin delivery system. More specifically, but not exclusively, the invention relates to an automatic insulin delivery system that comprises a feedforward control.

BACKGROUND OF THE INVENTION

In a person without diabetes, several systems including, for example, the metabolic, endocrine, and cardiovascular systems, function collectively to maintain homeostasis. However in a person with diabetes, the inherent glucose regulation mechanism is dysfunctional. Glucose levels are affected by the state of the metabolic-physiological-endocrine system. This includes factors such as insulin, stress, physical activity, hormonal levels, and fatigue. The effects of all these factors on blood glucose concentration (BGC) are highly complex and inter-related. In addition, factors such as food intake can cause glucose levels to change greatly and make glucose regulation and health management more difficult. These various factors are referred to as disturbances.

Insulin therapy involves multiple daily doses of insulin before meals or to correct high blood glucose, with the amount either pre-recommended by a physician or decided by the patient on the basis of measured BGC and the number of carbohydrates they estimate will be ingested at the time of the meal. This protocol is inconvenient and unreliable. It often results in hypoglycemic and/or hyperglycemic episodes, both of which can be life-limiting and life-threatening. Thus, there has been a desire to develop more optimized insulin delivery systems and protocols. This has included research to develop automatic insulin delivery systems.

The potential for successful automatic insulin delivery has entered a new era due to recent technological advancements of insulin pumps and blood glucose sensors. However, for full automation and control capable of reducing the variance in BGC, the control algorithm must be capable of tight control for major disturbances such as meals, activity, and stress. Theoretically, the superiority of feedforward control (FFC) over all other control systems is that corrective action can be taken to cancel the effects of disturbances on the control variable (i.e., BGC) proactively. FFC has not been capable of addressing the complexity of various input disturbances impacting the regulation of blood glucose levels associated with diabetes due to inadequacy of effective model development of the complex causative relationships of disturbances and the controlled variable. This is insufficient as it fails to determine accurately the insulin infusion rate to substantially eliminate the effects of the modeled disturbances.

While Feedback Control (FBC) and some model-based algorithms have shown promise and progress in real studies, there does not appear to be any clinical studies of an FFC or Feedback Feed Forward Control (FBFF) approach on real subjects in the literature. Actually, even from a search in the process control literature the successful implementation of FFC on real systems appears to be quite limited. This is likely due to the difficulty of developing accurate causal relationship of inputs on the controlled variable for real processes because of the existence of unmeasured disturbances and pairwise correlation of the inputs. Therefore, the objective of this work is the development of a subject-specific FFC modeling methodology under free-living data collection to effectively compensate for changes in meals, activity, and stress.

Consequently, there is a significant need for a system providing automatic delivery of insulin with minimal variability around the desired glucose target.

Accordingly, it is an objective of the claimed invention to provide a semi-coupled modeling network that presents a more phenomenological FFC law that includes input dynamics, unmeasured pseudo-blood insulin and blood glucose dynamics and blood glucose levels.

Other objects, advantages and features of the present invention will become apparent from the following specification taken in conjunction with the accompanying drawings.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF SUMMARY OF THE INVENTION

Therefore, it is a primary object, feature, and/or advantage of the invention to improve on and/or overcome the deficiencies in the art.

It is another object, feature, and/or advantage of the invention to provide and automatic insulin delivery system that includes an apparatus for administering insulin, a plurality of sensors, and a model that is stored on a machine readable non-transitory media that is associated with a computing device.

It is yet another object, feature, and/or advantage of the invention to provide a coupled model that applies a feedforward control It is a further object, feature, and/or advantage of the invention to provide an automatic insulin delivery system that includes a monitoring system comprising one or more sensors configured to monitor at least of the following variables: body position, movement, heat dissipated, skin temperature, near body temperature, galvanic skin response, sleep, basal insulin, and bolus insulin; and provide them as inputs to the model.

It is still a further object, feature, and/or advantage of the invention to provide an automatic insulin delivery system that allows a user to manually input variables related to Blood Insulin Concentration and/or Blood Glucose Concentration.

It is still yet a further object, feature, and/or advantage of the invention to provide an automatic insulin delivery system wherein the monitoring system includes one or more of the following types of sensors: a soft sensor, a remote sensor, an accelerometer, or a thermistor.

It is still yet a further object, feature, and/or advantage of the invention to provide a method of administering insulin as determined by a semi-coupled network utilizing a feedforward control.

It is still yet a further object, feature, and/or advantage of the invention to provide a method of administering insulin based on the following feedforward control:

$$f_x(X_t;\hat{\theta})|_{x_{1,t}} - B_t - (f_x(X_0;\hat{\theta}) - B_0) = f_x(X_t;\hat{\theta})|_{x_{1,t}} - f_x(X_0;\hat{\theta}) + B_0 - B_t = 0;$$

wherein $f_x(X_t;\hat{\theta})$ is a fitted function of input variables only, $X_t$ is a matrix of measured input variables, $\hat{\theta}$ is the vector of estimated parameters, and $B_t$ is the model bias at time t.

These and/or other objects, features, and advantages of the invention will be apparent to those skilled in the art. The invention is not to be limited to or by these objects, features and advantages. No single embodiment need provide each and every object, feature, or advantage.

BRIEF DESCRIPTION OF THE FIGURES

FIG. 9A shows the variability in BGC for Subject 11 over two weeks without feedforward or feedback feedforward control. FIG. 9B shows the variability in BGC for Subject 11 over two weeks with an exemplary FFC of the invention.

Figure 1:
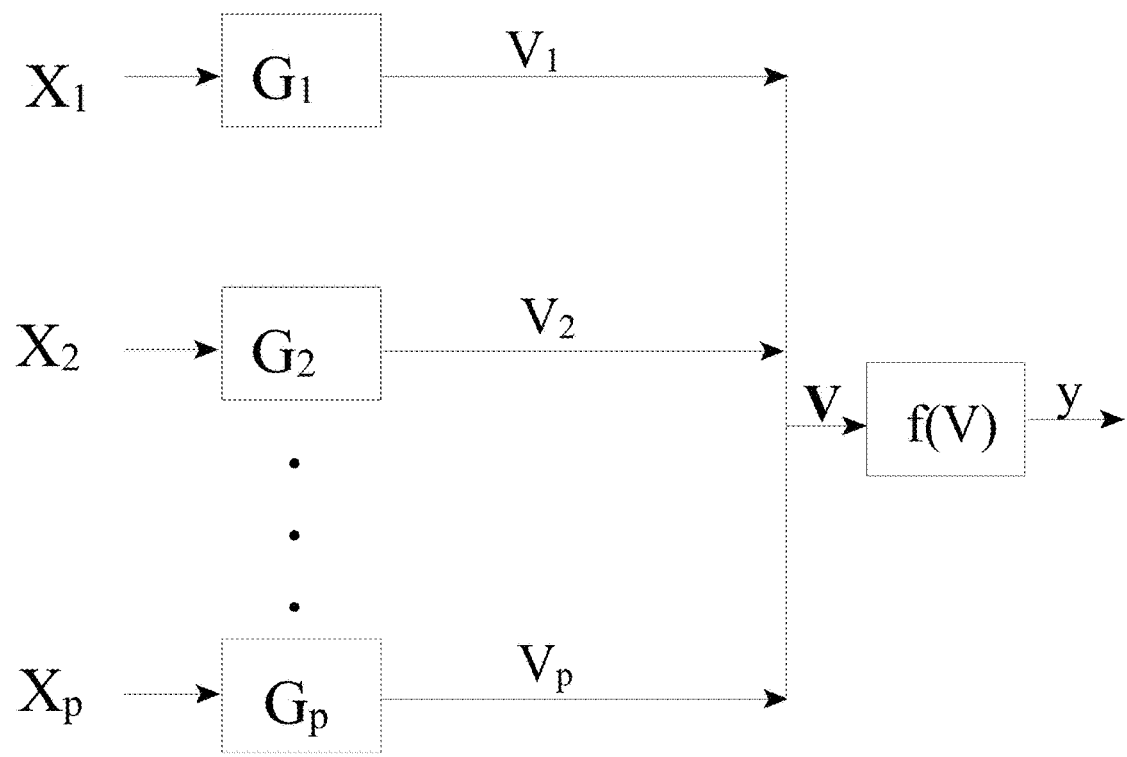
FIG. 1 is an exemplary block diagram for a general multiple-input, single-output Wiener network.

Various embodiments of the present invention are described in detail with reference to the drawings. The reference to various embodiments does not limit the scope of the invention. Figures represented herein are not limitations to the various embodiments according to the invention and are presented for exemplary illustration of the invention.

DETAILED DESCRIPTION OF THE INVENTION

The embodiments of this invention are not limited to particular insulin pumps, apparatuses for monitoring insulin and/or blood glucose levels, activity inputs, and stress measuring devices. It is further to be understood that all terminology used herein is for the purpose of describing particular embodiments only, and is not intended to be limiting in any manner or scope. For example, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

Definitions

As used herein the singular forms "a," "an" and "the" can include plural referents unless the content clearly indicates otherwise.

As used herein the term "BIC" refers to blood insulin concentration. It is not limited to any particular measurement unit.

As used herein the term "BGC" refers to blood glucose concentration. It is not limited to any particular measurement unit.

As used herein the term "FBC" refers to feedback control or any synonyms thereof, including for example, "feed-back control."

As used herein the term "FBFF" refers to a feedback feedforward control.

As used herein the term "FFC" refers to feedforward control or any synonyms thereof, including for example, "feed-forward control" and "feed forward control."

As used herein the term "WMM" refers to Wiener modeling method.

As used herein the term "CMM" refers to coupled modeling method.

Semi-Coupled Network

The invention employs a semi-coupled network 14 based on the Wiener modeling method. The Wiener modeling method provides feedforward controllers that contain input-specific numerator and denominator dynamics. However, the Wiener modeling method's structural limitations impact its ability to maintain high accuracy over a broad range. The semi-coupled network extends the Wiener modeling method's ability to address other types of static and dynamic behavior with unmeasured pseudo-BIC variable (while not wishing to be bound by the theory it is believe this role is for BIC, it may actually be a composite of species in the blood but predominately insulin). The use of the pseudo-BIC variable allows modeling on the blood directly and accounts for the interaction of glucose and insulin in the blood. This results in a novel feed forward controller that not only has input-specific numerator and denominator dynamics, but also blood glucose and pseudo-blood insulin dynamics as well as a dependence on the BGC.

In general, Wiener modeling follows a block-oriented model structure formed by a series and/or parallel arrangement of nonlinear static and linear dynamic blocks. A block diagram with p inputs and one output is given in FIG. 1.

In the Wiener network, the inputs are represented by $x_i$ where $i=1, \ldots, p$, which are the measured noninvasive variables or disturbances. Each input has its own linear dynamic block, $G_i$, and each dynamic block has an intermediate, unobservable output, $v_i$, which represents the independent dynamic response of its corresponding input. All the intermediate $v_i$'s are collected and passed through an unrestricted static gain block, $f(V)$, to produce the final output, y. If employed in BGC control system, $x_i$ represents things like food, activity, and stress, i.e., disturbances that affect BGC and the output variable y is BGC.

The Wiener network is suitable for the input transfer function model. However, it suffers from limitations in accounting for and controlling response. Thus, in the context of BGC, it is limited in representing the interaction of insulin and glucose in the blood. This drawback limits the Wiener modeling method's ability to develop an accurate physiological fit for BGC, which is critical to controller performance. To model blood insulin and glucose interaction, it is necessary to have BIC at the sampling rate of BGC. There is no sensor that is able to monitor this in existence currently. Thus, to circumvent this need, the invention employs a semi-coupled network for BIC and BGC, which led to the development of an unmeasured "pseudo" BIC variable. This resulted in a superior phenomenological for the dynamic relationship between insulin infusion rate, consumed nutrients, and BGC.

Figure 2:
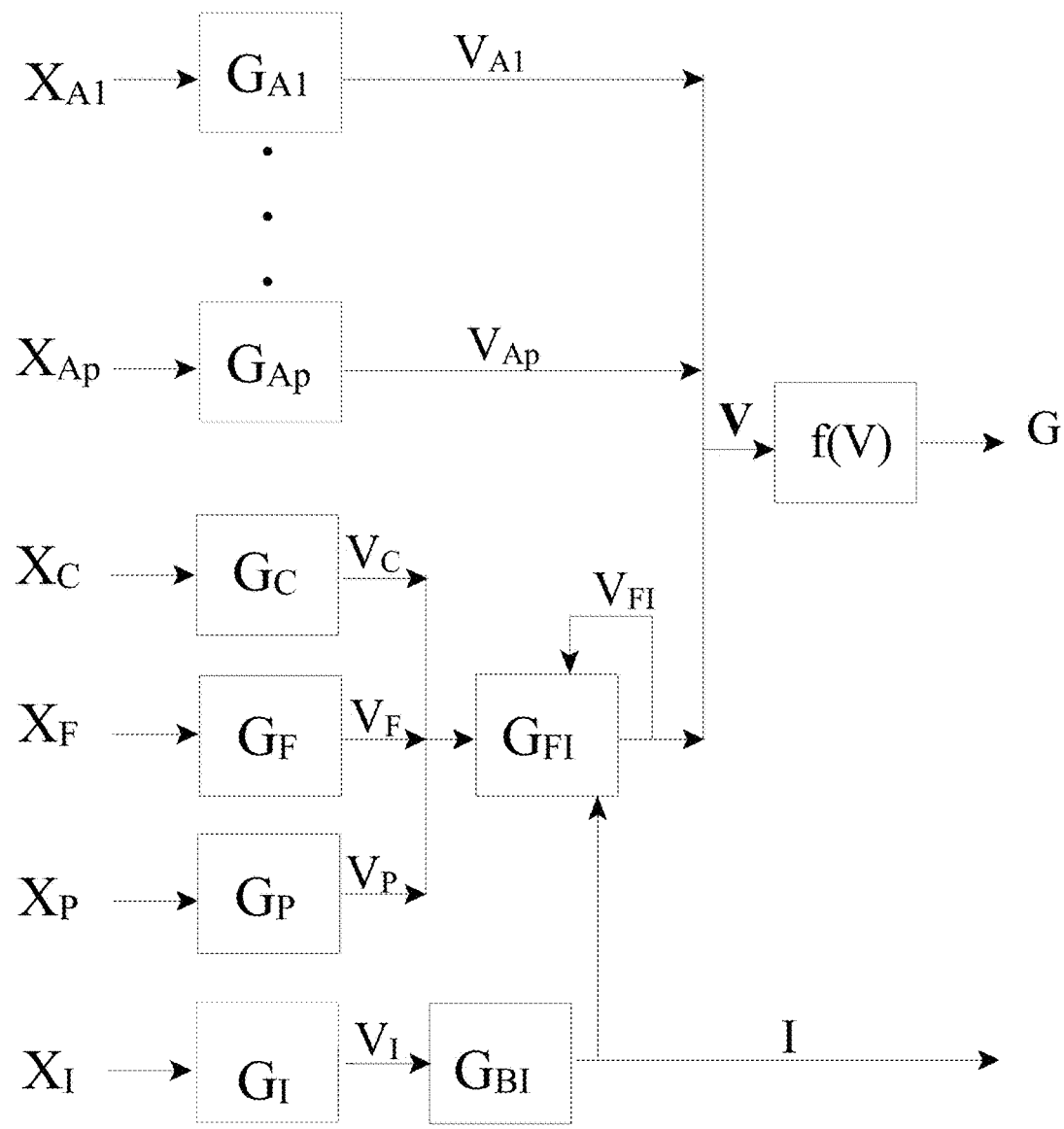
FIG. 2 is a block diagram of a semi-coupled network (Wiener/Coupled network) of the invention for pseudo-BIC and BGC with unlimited activity input variables.

A semi-coupled network of the invention is shown in FIG. 2. As shown in FIG. 2, all of the inputs, $x_i$, pass through a linear dynamic block to produce the unobservable dynamic output variables $v_i$ as in the Wiener modeling method. Note that, $i=A_1, \ldots A_p$, for the p activity inputs, C for carbohydrates, F for fats, P for proteins, and I for insulin. When the input for food is by meal size, these three blocks collapse into one block for the size of the meal (small, medium or large, for example). Thus, a benefit of certain embodiments of the invention is that it does not require detailed food logs and can be implemented based on meal size. A dynamic mass balance on the $G_{FI}$ block in FIG. 2 represents the BGC due to food and insulin only. The dynamic mass balance on the $G_{FI}$ block gives:

$$\frac{dV_{FI}(t)}{dt} = a_C v_C(t) + a_F v_{FC}(t) + a_P v_P(t) - a_{FI} I(t) V_{FI}(t) \quad (1)$$

where $a_C$, $a_F$, $a_P$, and $a_{FI}$ are estimable model parameters; I(t) is the unmeasured pseudo-BIC at time t; and $V_{FI}(t)$ is the BGC due to food and insulin changes only. Similarly, a dynamic mass balance on the $G_{BI}$ block, which represents BIC, gives:

$$\frac{dI(t)}{dt} = a_I v_I(t) - a_{BI} I(t) \quad (2)$$

where $a_I$ and $a_{BI}$, are estimable model parameters. The function $f(V)$ is called "the static function." This function can theoretically be of any form. For effectiveness under mild extrapolation, a first-order linear regression model can be used, given in discrete form as $$y_t = \eta_t + \varepsilon_t \quad (3)$$

where $$\eta_t = f(V_t) = G_t = a_0 + V_{FI} + a_{A_1} + \ldots + a_{A_p} v_{A_p,t} \quad (3a)$$

$y_t$ is the measured BGC at time t, $\varepsilon_t$ is the error term assumed to be independently normally distributed with mean 0 and variance $\sigma^2$ for all t, and $a_0$ and $a_{Ai}$ are static estimable model parameters. This allows the model to mildly extrapolate BGC outside of the input space.

Figure 3:
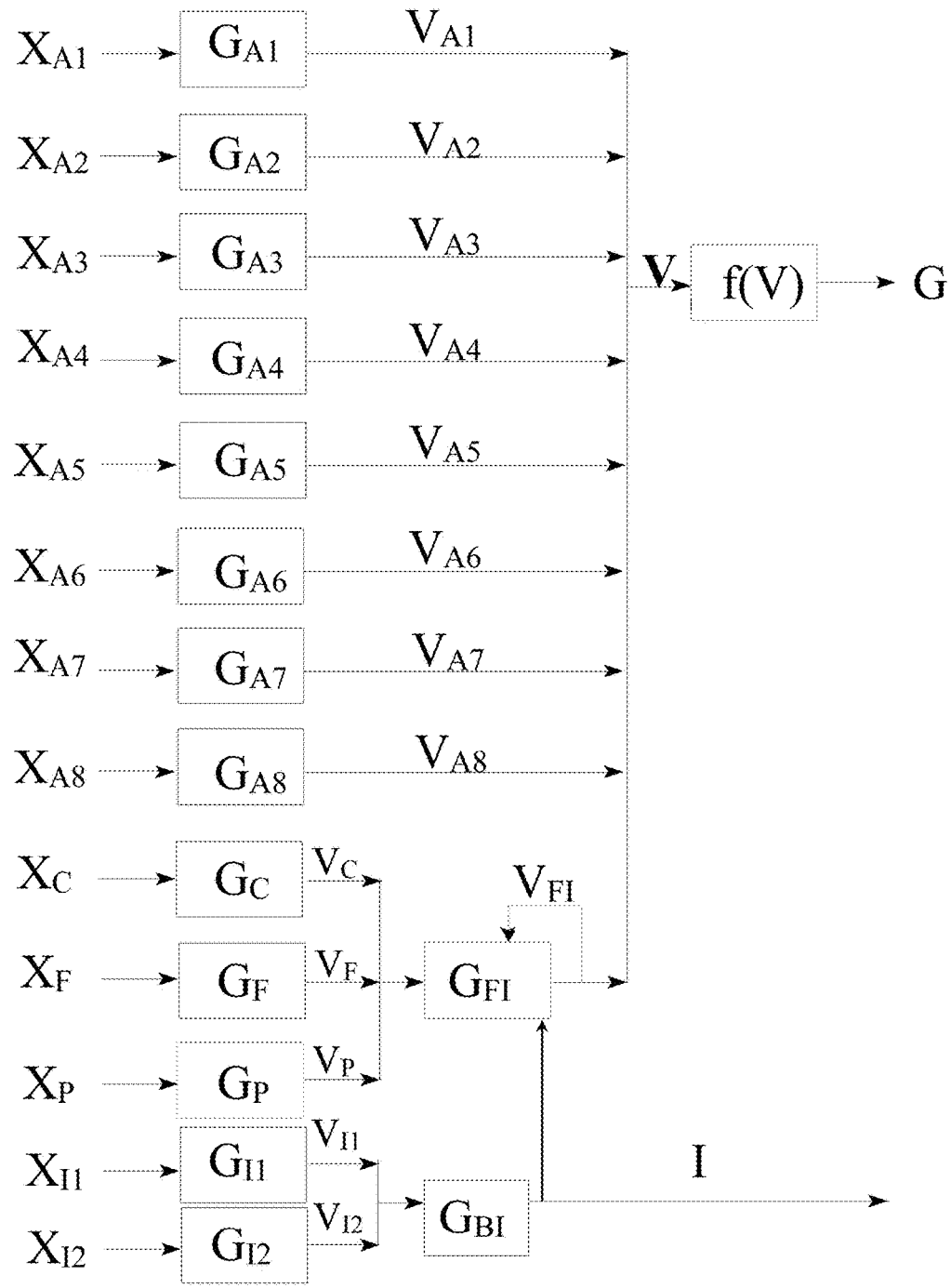
FIG. 3 is a block diagram of an exemplary semi-coupled network (Wiener/Coupled network) of the invention for BIC and BGC with thirteen input variables.

BGC is affected by many different disturbances. The three most significant noninvasive disturbances fall into one of three categories: insulin, consumed energy, and activities. To adequately control BGC through the semi-coupled network 14, each of these disturbances must be taken into account. FIG. 3 shows an exemplary semi-coupled network 14 of the invention accounting for thirteen inputs 16 (disturbances). This includes two insulin inputs, three consumed energy inputs, and eight activity inputs.

Insulin

There are two types of insulin: basal and bolus. Basal insulin, often referred to as background insulin, functions to keep blood glucose levels consistent during periods of fasting. Basal insulin is produced by the pancreas. Basal insulin can also be provided by the continuous administration of fast-acting insulin in small doses. Bolus insulin is faster acting insulin provided in some dosage. It can be administered intravenously, by intramuscular injection, by intrathecal injection, or by subcutaneous injection. In FIG. 3, these are accounted for by $X_I$, in particular, $X_{I1}$ and $X_{I2}$. As shown in FIG. 3, the insulin inputs combine to form the $G_{BI}$ block (previously represented in Formula 2), which feeds into the $G_{FI}$ block (previously represented in Formula 1). The $G_{FI}$ block also contains the output from the consumed energy inputs.

Consumed Energy

There are three main categories of consumed energy: carbohydrates, fats, and proteins. As shown in FIGS. 2 and 3, these are accounted for by $X_C$, $X_F$, and $X_P$. The consumed energy outputs feed into the $G_{FI}$ block along with the output from the $G_{BI}$ block. The output from the $G_{FI}$ block then combines with the activity disturbances.

Activities

There are many activities that affect BGC. These activities include, but are not limited to, body position, movement, heat dissipated, skin temperature, near body temperature, galvanic skin response, and sleep. In order to monitor body position and movement, it is preferable to use a two-axis accelerometer. Sleep can be monitored by the circadian rhythm. The heat dissipated from the body can be accounted for based on the body's heat flux. Skin temperature and near-body temperature can be measured by sensitive thermistors. Galvanic skin response (GSR) can be measured by the conductivity of a person's skin as it varies due to physical and emotional stimuli. The monitored activities are then combined with the output from the $G_{FI}$ block output V, as shown in FIG. 3. Further, $V_{FI}$ provides feedback into $G_{FI}$.

Any type and number of monitoring systems can be used to monitor the various activities. In a preferred embodiment, a single monitoring system is employed to monitor all activities at once. A preferred monitoring system is SenseWear® Pro3 Body Monitoring System, available from BodyMedia, Inc. in Pittsburgh, Pa.

Feedback-Feedforward Control

In a preferred embodiment the semi-coupled network 14 is used in a FBFF process control scheme. This is because FFC proactively nullifies measured modeled disturbances prior to the disturbance affecting the system. FBC addresses unmeasured disturbances, modeling and measurement errors. Thus, in the context of BGC, it is ideal to employ a process control having both FFC and FBC. This will provide a process control capable of both nullifying measured disturbances before they affect the system and compensating for any disturbances not adequately handled by FFC.

Feedforward Control Law

Due to its complexity, the implementation of the coupled-model method 14 requires a novel FFC law and its solution at each sampling time to obtain the contribution of FFC to the insulin infusion rate at each sampling time. The innovation in the FFC law is given in Equation 4 below:

$$f_x(X_t;\hat{\theta})|_{x_{I,t}} - B_t - (f_x(X_0;\hat{\theta}) - B_0) = f_x(X_t;\hat{\theta})|_{x_{I,t}} - f_x(X_0;\hat{\theta}) + B_0 - B_t = 0 \quad (4)$$

where $f_x(X_t; \hat{\theta})$ is a fitted function of input variables only (more specifically, no outputs); $X_t$ is a matrix of measured input variables; $\hat{\theta}$ is the vector of estimated parameters; and; $B_t$ is the model bias at time t. Note that, $Y^{set} = f_x(X_0; \hat{\theta}) - B_0$, where $Y^{set}$ is the target value of the controlled variable (i.e., the set point). For the input variables that are measured, with a perfect model for this set of inputs, this FFC law states mathematically the value of the manipulated variable, in this context $x_{I,t}$, the insulin infusion rate at t, to offset all these input changes at t.

Thus, at each time instant, Equation 4 determines the value of $x_{I,t}$ for $f_x(X_t; \hat{\theta}) - B_t$ to remain at $Y^{set}$. The current approach to obtain this value requires linearization of $f_x(X_t; \hat{\theta})$, transformation to the Laplace domain, separation of each input into a separate FFC component system, approximations to make all the component controllers physically realizable, and a solution to each component that are added to give the FFC output. The innovation of this approach does not require any of these approximations, transformations, or solutions. As Equation 4 shows, obtaining the FFC output is a matter of the finding the root of $x_{I,t}$ that satisfies Equation 4 at each time instant. For any network, including the semi-couple network here, using finite difference approximations for the derivatives, the network equations are solved simultaneously to obtain $v_{I,t}$ and then $x_{I,t}$ by inverting $v_{I,t}$. For example, if $G_I$ is a first order transfer function, i.e., $$\tau_I \frac{dv_I(t)}{dt} + v_I(t) = x_I(t) \quad (5)$$

then $\tau_I \frac{v_{I,t} - v_{I,t-\Delta t}}{\Delta t} + v_{I,t} \approx x_{I,t-\Delta t}$ $$\Rightarrow v_{I,t} \approx \frac{\tau_I}{\tau_I + \Delta t} v_{I,t-\Delta t} + \frac{\Delta t}{\tau_I + \Delta t} x_{I,t-\Delta t} = \quad (6)$$

$$\delta_{I,1} v_{I,t-\Delta t} + \omega_{I,1} x_{I,t-\Delta t} = \delta_{I,1} v_{I,t-\Delta t} + (1 - \delta_{I,1}) x_{I,t-\Delta t}$$

and from inverting Equation 6, the solution to Equation 3 in this example is expressed as $$x_{I,t} = \tau_I \frac{v_{I,t} - v_{I,t-\Delta t}}{\Delta t} + v_{I,t} \quad (7)$$

Thus, an innovation is that an approximation to meet the requirement of a physical realizable solution is not an issue for this approach. More specifically, Equation 7 gives the insulin infusion rate at each time instant to satisfy Equation 3 and an assumption to meet a condition of physically realizable is not needed.

The innovation to estimate the $B_t$ is the following equation.

$$B_t = f(V_{t-\Delta t}) - y_{t-\Delta t} \quad (8)$$

Method of Controlling Insulin

The process control of the invention can be employed in the monitoring and regulation of BGC for patients, particularly patients suffering from type 1 diabetes mellitus. The process control scheme of the invention employs an insulin delivery system 4, a computing device 8 comprising a processor 10, machine readable non-transitory media 12 which stores the coupled-model 14 of the invention, and a monitoring system 2.

Figure 4:
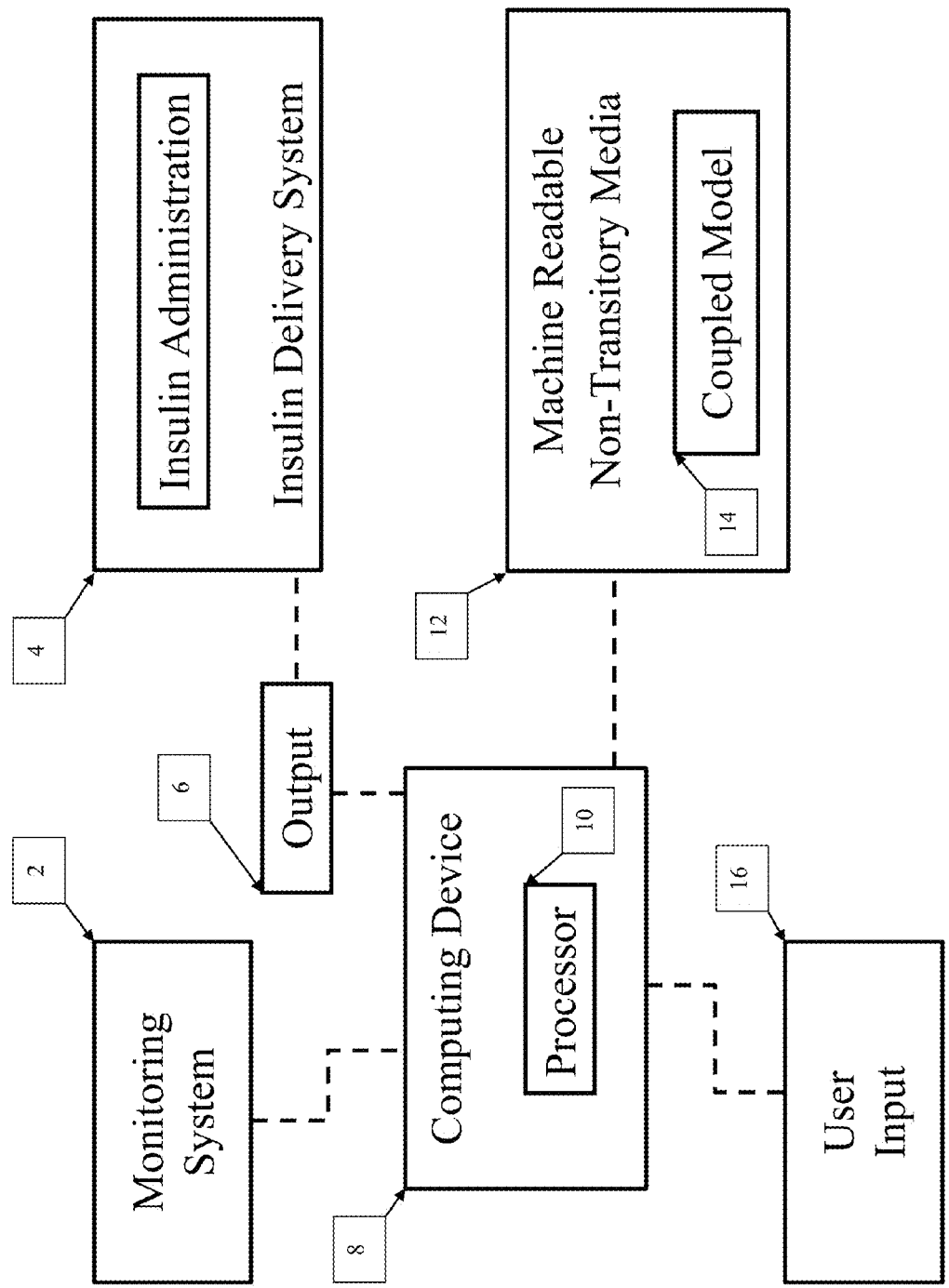
FIG. 4 shows a diagram of a system or method for controlling BGC according to the invention.

FIG. 4 shows an exemplary method of controlling BGC according to the invention. The method employs a monitoring system 2, which monitors the various inputs (disturbances). For example, the monitoring system can provide information regarding the activity inputs ($X_A$ in FIGS. 2 and 3), such as, skin temperature, near body temperature, and galvanic skin response. The monitoring system 2 can comprise one or more sensors capable of monitoring one of more of the inputs. In an aspect of the invention, the system can include a soft or virtual sensor monitoring, such as, heat flux. In an embodiment of the invention, the patient's basal and bolus insulin ($X_I$ in FIG. 2; $X_{I1}$ and $X_{I2}$ in FIG. 3) can be monitored by the monitoring system 2. For example, the basal insulin can be read by any automatic system for monitoring blood glucose. Additionally, as bolus insulin can be administered by the insulin delivery system 4 and as the amount can be directed by the computing device 8, the amount of bolus insulin can be automatically monitored.

FIG. 4 further shows the method also employs user input data 16. The user input 16 can include consumed energy and blood glucose levels. When providing consumed energy, the consumed energy can be provided based on size of a meal (for example, small meal, medium meal, or large meal), based on actual or estimated energy intake (for example, 250 calories, 25 grams of fat, 12 grams of protein), or based on identification of food items (for example, selection from a menu of items: apple slices, buttered toast, etc.). In FIGS. 2 and 3 these data are represented by $X_C$, $X_F$, and $X_P$. In certain embodiments of the invention the blood glucose levels can be taken manually and the user can input 16 the data. In FIG. 2 this data is represented by $X_I$. In FIG. 3 this data is represented by $X_{I1}$ and $X_{I2}$ representing basal and bolus insulin.

As shown in FIG. 4, both the user input 16 and monitoring system 2 are in operable communication with a computing device 8 that contains a processor 10. The computing device 8 is also in operable communication with a machine readable non-transitory media 12. The machine readable non-transitory media 12 can store the coupled model 14. The inputs 16, 2 are parametrized by the coupled-model 14 to provide an output 6 that directs the insulin delivery system 4. It is to be understood that wireless transceivers may be used to communicate information from sensors to the computing device 8. The sensors may be associated with wearable devices, mobile devices, or other computing devices.

Figure 5:
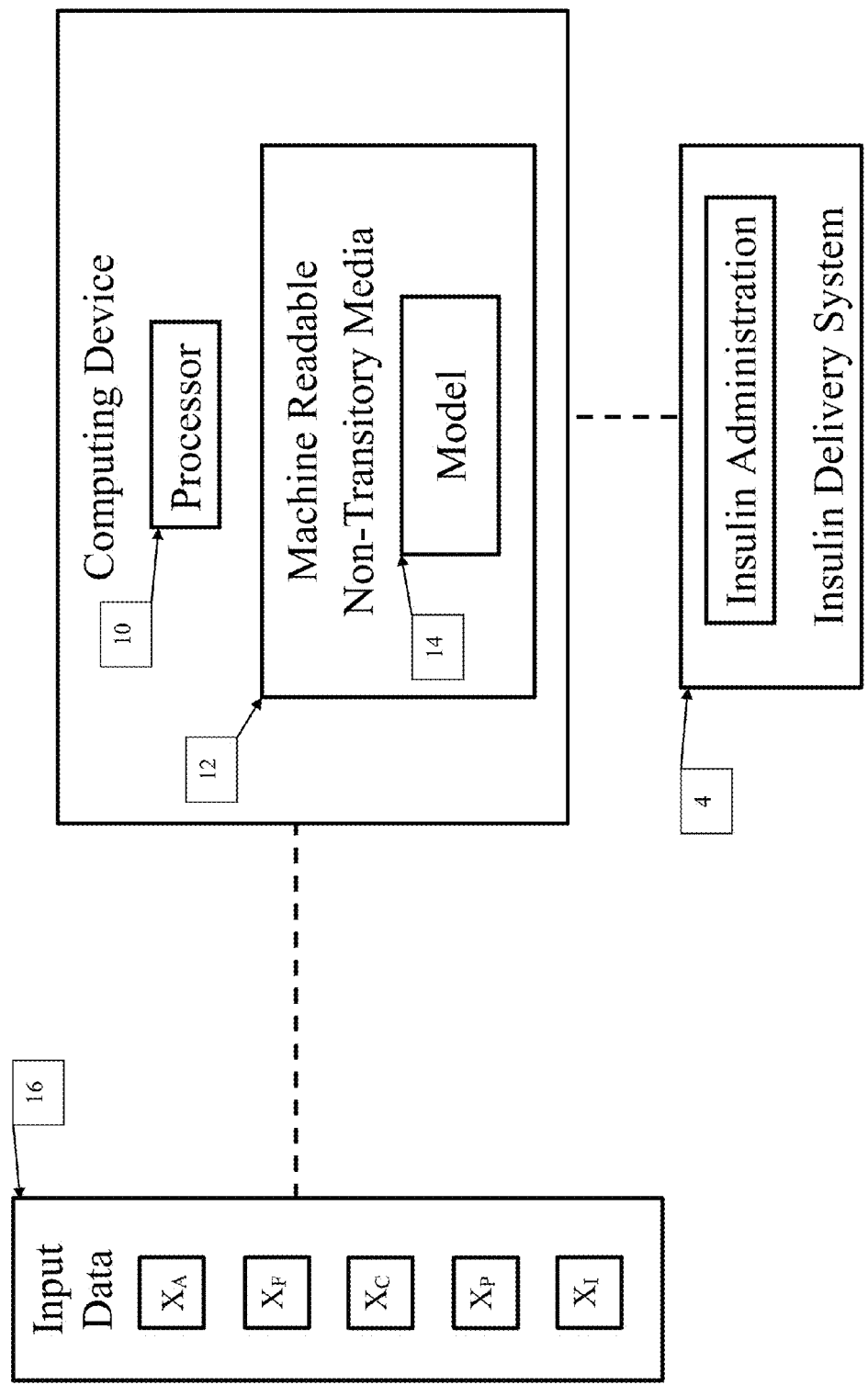
FIG. 5 shows a diagram of system or method for controlling BGC according to the invention.

FIG. 5 shows another embodiment of the invention where the computing device comprises both a processor 10 and the machine readable non-transitory media 12. The computing device 8 is in operable communication with the inputs 16, 2 and the insulin delivery system 4. In embodiments of the invention shown in FIG. 5, the inputs 16, 2 can include automatically monitored inputs (such as activity inputs which are monitored by a monitoring system 2) and the inputs 16, 2 can include manually entered inputs 16 (such as consumed energy or insulin levels).

FIGS. 4 and 5 show the computing device 8 is also in operable communication with an insulin delivery system 4. The insulin deliver system 4 can comprises an apparatus suitable for administering insulin. Any suitable apparatus for administering insulin can be employed, including, but not limited to, an automatic insulin pump, a remotely controlled insulin pump, an IV, or a catheter. Any suitable insulin pump capable of communication with the control system can be used. Preferably, the control method of the invention is uses a remotely controlled insulin pump. Selection of an insulin pump can be based on preferences of the user for other features. The user inputs 16 and inputs provided by the monitoring system 2 are parametrized by the model 14 stored on the machine readable non-transitory media 12, which is in operable communication with the computing device 8. The model 14 provides an output to the computing device 8 which in turn provides an output 6 (as shown in FIG. 4) to the insulin delivery system 4, which can direct the insulin delivery system 4 to nullify and/or compensate for measured disturbances via the feedforward control scheme and all causes for feedback error including unmeasured disturbances to the BGC by the administration of insulin. In some embodiments of the invention, the output 6 can be provided in any communicable form and recorded, printed, displayed, etc. such that there is a record of the output 6. In an embodiment of the invention where the basal and bolus insulin are automatically monitored the output 6 can be relayed back into the machine readable non-transitory media 12.

Embodiments of the invention can reduce the variance in blood glucose concentration of a patient by proactively nullifying one or more disturbances on the patient's blood glucose system. In embodiments of the invention, when compared with existing methods of controlling blood glucose concentration, the reduction in variance can be greater than 50%, preferably greater than 60%, and more preferably greater than 70%.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

The use of free-living data presents the challenge of not over-fitting the data in the presence of unmeasured disturbances and cross correlation of measured inputs. This challenge was addressed through the innovative development and use of nonlinear parameterized discrete-time physically based transfer functions and the method of cross validation, which splits the data into three sets: Training, Validation, and Testing.

The transfer functions are essentially linear ordinary differential equations; a second-order-plus-lead-plus-dead-time (SOPLDT) form is shown in Eq. 9.

$$\tau_i^2 \frac{d^2 v_i(t)}{dt^2} + 2\tau_i \zeta_i \frac{d v_i(t)}{dt} + v_i(t) = \tau_{ai} \frac{d x_i(t)}{dt} + x_i(t) \quad (9)$$

where $i=1, \ldots, p$, p is the total number of inputs, $\tau_i$ is the time constant, $\zeta_i$ is the damping coefficient, $\tau_{ai}$ is the lead parameter and $\theta_i$ is the dead time. Using a backward difference approximation applied to a sampling interval of $\Delta t$, an approximate discrete-time form of Eq. 9 given below by Eq. 10:

$$v_{i,t} = \delta_{i,1} v_{i,t-\Delta t} + \delta_{i,2} v_{i,t-2\Delta t} + \omega_{i,1} x_{i,t-\Delta t} + \omega_{i,2} x_{i,t-2\Delta t} \quad (10)$$

where $$\delta_{i,1} = \frac{2\tau_i^2 + 2\tau_i \zeta_i \Delta t}{\tau_i^2 + 2\tau_i \zeta_i \Delta t + \Delta t^2} \quad (11)$$

$$\delta_{i,2} = \frac{-\tau_i^2}{\tau_i^2 + 2\tau_i \zeta_i \Delta t + \Delta t^2} \quad (12)$$

$$\omega_{i,1} = \frac{(\tau_{ai} + \Delta t)\Delta t}{\tau_i^2 + 2\tau_i \zeta_i \Delta t + \Delta t^2} \quad (13)$$

and $$\omega_{i,2} = 1 - \delta_{i,1} - \delta_{i,2} - \omega_{i,1} \quad (14)$$

to satisfy the constraint of unity gain, and $x_{i,t}$ is the value of the ith input at t. Two additional physical constraints are $\tau_i > 0$ and $\zeta_i > 0$, $\forall i$. Note that, for each $v_{i,t}$, the parameters (i.e., $\delta_{1,i}$, $\delta_{2,i}$, $\omega_{1,i}$, $\omega_{2,i}$) in Eq. 10 are determined from highly nonlinear functions of the continuous-time dynamic parameters, $\tau_{ai}$, $\tau_i$, and $\zeta_i$, via Eqs. 11-14.

The model parameters are estimated using the Training data, which is usually the largest set. The Validation set is used to guard against over-fitting, as the final set of parameters must maximize the fit in this set. Since these two sets influence the parameter estimation process, the Testing set is used as a final check on model fit, as the data in this set has no influence on the values of the estimated parameters. To achieve the best fit possible, the present invention follows the cross validation process of the Wiener modeling method (WMM) which seeks to maximize fit in the training data set and obtain comparable, or similar, fit in the other two sets. Following the cross validation strategy of the WMM, the present invention develops a novel procedure to estimate the model parameters in the coupled modeling method (CMM) under the least squares criterion that decomposes the problem as further discussed. First, all the coupled parameters are estimated under a fixed set of dynamic parameters for the nutrient variables, with $a_{41}$ to $a_{4p}$ set to zero, without the presence of activity variables. Next, the dynamic parameters for each activity variable are estimated individually with $V_{FI}$ set to 0. After obtaining the dynamic parameters for each activity variable, the static model coefficients are estimated.

According to the aforementioned modeling structure of the present invention, 13 variables were input into the system as described in Table 1, as broken down into the categories of food disturbances, activity disturbances, and insulin infusion variables.

TABLE 1

| Food Variables | Activity Variables | Insulin Variables |
|---|---|---|
| Carbohydrates | Traverse accel-peaks | Bolus |
| Fats | Heat flux-average | Basal |
| Proteins | Longitudinal accel-average | |
| | Near Body Temperature | |
| | Traverse accel-MAD | |
| | GSR-average | |
| | Energy Expenditure | |
| | Time of Day | |

The activity variables were collected using the SenseWear® Pro3 Body Monitoring System, available through BodyMedia Inc. This device is worn on the triceps of the subject's arm. The SenseWear® armband utilizes pattern detection algorithms that employ physiologic signals from a unique combination of sensors to generate values for activity variables and samples at a rate of once per minute, however, measurements at five minute intervals were used to match the sampling rate of the continuous glucose monitor system.

Data were collected in three different sets. The "Training" data set was used to estimate model parameters. The "Validation" data set was used to stop the convergence process of the estimation procedure of the "Training" data and to guard against over-fitting the model. The goal of the model is to stop the estimation process when a high $r_{fit}$ is obtained on the "Validation" data given that its value was close to the "Training" value. The "Testing" data set represents data not used in any way to influence the fitting of the model. Results are shown in Tables 2-5.

TABLE 2

WWM and CMM Part 1 Study results with all the inputs under one week of training and one week of validation. The units for AD and AAD are mg/dL.

| Subject | Method | Days | Training | | | Validation | | |
|---|---|---|---|---|---|---|---|---|
| | | | AD | AAD | $r_{fit}$ | AD | AAD | $r_{fit}$ |
| 1 | WMM | 14.0 | 0.0 | 44.8 | 0.61 | 20.4 | 50.5 | 0.68 |
| 2 | WMM | 13.0 | 0.0 | 72.1 | 0.49 | −18.0 | 68.5 | 0.51 |
| 3 | WMM | 13.9 | 0.0 | 48.0 | 0.68 | −0.1 | 49.3 | 0.66 |
| 4 | WMM | 10.7 | 0.0 | 31.6 | 0.53 | 33.4 | 48.4 | 0.55 |
| 5 | WMM | 14.0 | 0.0 | 62.6 | 0.56 | 15.1 | 73.6 | 0.55 |
| 6 | WMM | 13.9 | 0.0 | 50.1 | 0.67 | 24.9 | 45.6 | 0.68 |
| 7 | WMM | 14.0 | 0.0 | 46.7 | 0.69 | 37.1 | 56.5 | 0.64 |
| 8 | WMM | 14.0 | 0.0 | 32.7 | 0.45 | 10.8 | 43.2 | 0.43 |
| 9 | WMM | 13.9 | 0.0 | 51.8 | 0.63 | −35.2 | 64.2 | 0.56 |
| 10 | WMM | 16.8 | 0.0 | 47.4 | 0.57 | 14.0 | 46.8 | 0.73 |
| 11 | WMM | 15.1 | 0.0 | 33.7 | 0.72 | −24.3 | 47.2 | 0.79 |
| 12 | WMM | 8.9 | 0.0 | 56.3 | 0.63 | −33.0 | 83.0 | 0.72 |
| 13 | WMM | 8.2 | 0.3 | 55.4 | 0.54 | 52.5 | 76.9 | 0.58 |
| 14 | WMM | 7.9 | −0.1 | 48.2 | 0.56 | −30.1 | 48.6 | 0.61 |
| 15 | WMM | 13.6 | 0.0 | 23.1 | 0.56 | 20.7 | 45.2 | 0.56 |
| Avg of Absolute Value | WMM | 12.8 | 0.0 | 47.0 | 0.59 | 21.2 | 56.5 | 0.62 |
| 1 | CMM | 14.0 | 1.1 | 43.5 | 0.65 | 32.2 | 57.4 | 0.64 |
| 2 | CMM | 13.0 | −0.4 | 57.8 | 0.73 | −44.6 | 66.4 | 0.71 |
| 3 | CMM | 13.9 | −0.1 | 51.7 | 0.62 | −40.6 | 58.8 | 0.62 |
| 4 | CMM | 10.7 | −0.1 | 29.9 | 0.62 | 59.8 | 63.8 | 0.56 |
| 5 | CMM | 14.0 | 0.3 | 63.3 | 0.60 | 24.7 | 70.8 | 0.58 |
| 6 | CMM | 13.9 | −0.5 | 49.9 | 0.67 | 31.7 | 49.0 | 0.67 |
| 7 | CMM | 14.0 | 0.3 | 44.8 | 0.71 | −53.8 | 69.5 | 0.63 |
| 8 | CMM | 14.0 | 0.9 | 32.8 | 0.42 | 12.6 | 43.3 | 0.48 |
| 9 | CMM | 13.9 | 6.3 | 54.3 | 0.60 | −9.2 | 52.5 | 0.59 |

TABLE 2-continued

WWM and CMM Part 1 Study results with all the inputs under one week of training and one week of validation. The units for AD and AAD are mg/dL.

| Subject | Method | Days | Training | | | Validation | | |
|---|---|---|---|---|---|---|---|---|
| | | | AD | AAD | $r_{fit}$ | AD | AAD | $r_{fit}$ |
| 10 | CMM | 16.8 | 0.0 | 43.5 | 0.68 | 15.9 | 48.3 | 0.68 |
| 11 | CMM | 15.1 | 0.2 | 29.8 | 0.82 | −37.1 | 60.4 | 0.85 |
| 12 | CMM | 8.9 | 1.3 | 55.6 | 0.66 | −39.8 | 72.8 | 0.76 |
| 13 | CMM | 8.2 | 0.0 | 49.4 | 0.67 | 48.5 | 74.3 | 0.61 |
| 14 | CMM | 7.9 | −0.2 | 45.3 | 0.60 | −5.4 | 41.9 | 0.61 |
| 15 | CMM | 13.6 | 2.3 | 23.4 | 0.56 | 21.2 | 46.0 | 0.57 |
| Avg of Absolute Value | CMM | 12.8 | 0.9 | 45.0 | 0.64 | 31.8 | 58.4 | 0.64 |

TABLE 3

WWM and CMM Part 1 Study results without armband inputs under one week of training and one week of validation. The units for AD and AAD are mg/dL.

| Subject | Method | Days | Training | | | Validation | | |
|---|---|---|---|---|---|---|---|---|
| | | | AD | AAD | $r_{fit}$ | AD | AAD | $r_{fit}$ |
| 1 | WMM | 14 | 0 | 49.2 | 0.52 | 26.9 | 56.8 | 0.57 |
| 2 | WMM | 13 | 0 | 65.4 | 0.58 | −13.1 | 64.4 | 0.56 |
| 3 | WMM | 13.9 | 0 | 61 | 0.46 | 18.2 | 56.6 | 0.42 |
| 4 | WMM | 10.7 | 0 | 32.2 | 0.48 | 32.6 | 32.6 | 0.49 |
| 5 | WMM | 14 | 0 | 66.1 | 0.5 | 11.3 | 81.7 | 0.44 |
| 6 | WMM | 13.9 | 0 | 62.8 | 0.39 | 13.9 | 50.8 | 0.35 |
| 7 | WMM | 14 | 0 | 58.3 | 0.52 | 21.3 | 51.5 | 0.57 |
| 8 | WMM | 14 | 0 | 35.8 | 0.25 | 15.1 | 46.6 | 0.34 |
| 9 | WMM | 13.9 | 0 | 59.3 | 0.52 | −21.8 | 64.4 | 0.43 |
| 10 | WMM | 16.8 | 0 | 48.8 | 0.55 | 13.3 | 49.8 | 0.67 |
| 11 | WMM | 15.1 | 0 | 33.5 | 0.7 | −23.5 | 48.3 | 0.77 |
| 12 | WMM | 8.9 | 0.2 | 58.4 | 0.61 | −37.6 | 87.7 | 0.61 |
| 13 | WMM | 8.2 | 0 | 61.5 | 0.4 | 54.9 | 82 | 0.45 |
| 14 | WMM | 7.9 | −0.1 | 48.2 | 0.56 | −30.1 | 48.6 | 0.61 |
| 15 | WMM | 13.6 | 0 | 25.2 | 0.5 | 26.4 | 45.5 | 0.5 |
| Avg of Absolute Value | WMM | 13.9 | 0 | 52 | 0.5 | 19.2 | 54.9 | 0.51 |
| 1 | CMM | 14 | 4 | 49.4 | 0.55 | 26.8 | 66.4 | 0.51 |
| 2 | CMM | 13 | 13.8 | 60.2 | 0.68 | −31.6 | 64.1 | 0.66 |
| 3 | CMM | 13.9 | 1.5 | 60.3 | 0.44 | −5 | 55.9 | 0.41 |
| 4 | CMM | 10.7 | −2.3 | 31.5 | 0.58 | 65.9 | 68.7 | 0.52 |
| 5 | CMM | 14 | 0.2 | 68.4 | 0.5 | 0.1 | 75.9 | 0.53 |
| 6 | CMM | 13.9 | −0.1 | 58.9 | 0.51 | 20.9 | 49.3 | 0.51 |
| 7 | CMM | 14 | 3.8 | 54.2 | 0.59 | −53.2 | 69.4 | 0.58 |
| 8 | CMM | 14 | −0.1 | 34.9 | 0.35 | 14.5 | 46.3 | 0.3 |
| 9 | CMM | 13.9 | 1.1 | 62.7 | 0.5 | −53.4 | 78 | 0.48 |
| 10 | CMM | 16.8 | 0 | 45 | 0.65 | 23.6 | 52.2 | 0.64 |
| 11 | CMM | 15.1 | 1.1 | 29.7 | 0.81 | −30.4 | 58.2 | 0.81 |
| 12 | CMM | 8.9 | 0 | 56.9 | 0.65 | −52.5 | 81.4 | 0.71 |
| 13 | CMM | 8.2 | 0 | 59 | 0.47 | 68 | 87.5 | 0.56 |
| 14 | CMM | 7.9 | 0 | 45.3 | 0.6 | −5.4 | 41.9 | 0.61 |
| 15 | CMM | 13.6 | −2.6 | 24.6 | 0.54 | 10.9 | 45.8 | 0.5 |
| Avg of Absolute Value | CMM | 13.9 | 2.6 | 50.5 | 0.56 | 29.6 | 62.2 | 0.54 |

TABLE 4

WWM and CMM Part 1 Study results with all the inputs under one week of training, four days of validation, and 3 days of testing. The units for AD and AAD are mg/dL.

| | | | 7 Day Training | | | 4 Day Validation | | | 3 Day Testing | | |
|---|---|---|---|---|---|---|---|---|---|---|---|
| Subject | Method | Days | AD | AAD | $r_{fit}$ | AD | AAD | $r_{fit}$ | AD | AAD | $r_{fit}$ |
| 1 | WMM | 14.0 | 0.0 | 45.0 | 0.60 | 20.1 | 52.9 | 0.66 | 16.7 | 46.9 | 0.66 |
| 2 | WMM | 13.0 | 0.0 | 67.2 | 0.57 | −33.3 | 62.6 | 0.67 | 2.9 | 64.8 | 0.54 |
| 3 | WMM | 13.9 | 0.0 | 50.9 | 0.64 | −12.9 | 60.7 | 0.53 | −21.3 | 53.0 | 0.68 |
| 4 | WMM | 10.7 | 0.0 | 31.9 | 0.53 | 31.1 | 52.5 | 0.52 | 35.4 | 40.5 | 0.57 |
| 5 | WMM | 14.0 | 0.0 | 63.3 | 0.55 | 31.4 | 87.3 | 0.54 | −15.0 | 55.9 | 0.67 |
| 6 | WMM | 13.9 | 0.0 | 52.8 | 0.65 | 37.9 | 59.8 | 0.60 | −0.1 | 34.0 | 0.60 |
| 7 | WMM | 14.0 | 0.0 | 56.4 | 0.56 | 25.6 | 52.6 | 0.58 | −1.7 | 58.7 | 0.56 |
| 8 | WMM | 14.0 | 0.0 | 36.5 | 0.21 | 26.7 | 46.1 | 0.28 | −0.1 | 48.7 | 0.30 |
| 9 | WMM | 13.9 | 0.0 | 53.2 | 0.61 | −19.4 | 51.8 | 0.65 | −54.9 | 75.8 | 0.55 |
| 10 | WMM | 16.8 | 0.0 | 44.9 | 0.62 | 15.0 | 43.6 | 0.68 | 0.8 | 50.9 | 0.70 |
| 11 | WMM | 15.1 | 0.0 | 30.4 | 0.79 | −22.3 | 41.8 | 0.81 | −25.3 | 60.8 | 0.63 |
| Avg of Absolute Value | WMM | 13.9 | 0.0 | 48.4 | 0.58 | 25.1 | 55.6 | 0.59 | 15.8 | 53.6 | 0.59 |
| 1 | CMM | 14.0 | 18.2 | 45.9 | 0.71 | 35.7 | 45.9 | 0.78 | 51.5 | 64.8 | 0.71 |
| 2 | CMM | 13.0 | 2.3 | 57.7 | 0.73 | −51.9 | 65.8 | 0.74 | −28.8 | 58.4 | 0.70 |
| 3 | CMM | 13.9 | −4.9 | 52.0 | 0.63 | −29.8 | 66.8 | 0.54 | 5.0 | 51.9 | 0.51 |
| 4 | CMM | 10.7 | 0.7 | 30.2 | 0.62 | 58.3 | 64.6 | 0.52 | 64.6 | 65.3 | 0.47 |
| 5 | CMM | 14.0 | 1.0 | 51.9 | 0.71 | 19.7 | 74.3 | 0.60 | −54.8 | 76.8 | 0.61 |
| 6 | CMM | 13.9 | 0.8 | 58.0 | 0.53 | −9.8 | 56.5 | 0.61 | −11.3 | 37.4 | 0.55 |
| 7 | CMM | 14.0 | 0.6 | 47.4 | 0.68 | −24.5 | 54.8 | 0.58 | −75.4 | 82.6 | 0.76 |
| 8 | CMM | 14.0 | 0.4 | 33.3 | 0.44 | 15.2 | 41.0 | 0.46 | −17.6 | 47.9 | 0.56 |
| 9 | CMM | 13.9 | 3.4 | 55.3 | 0.61 | −15.0 | 59.2 | 0.53 | −80.8 | 99.1 | 0.49 |
| 10 | CMM | 16.8 | 0.4 | 45.2 | 0.63 | 21.1 | 42.3 | 0.75 | 21.1 | 52.4 | 0.65 |
| 11 | CMM | 15.1 | −0.1 | 30.9 | 0.79 | −70.2 | 73.4 | 0.83 | −100.1 | 108.6 | 0.63 |
| Avg of Absolute Value | CMM | 13.9 | 3.0 | 46.2 | 0.64 | 31.9 | 58.6 | 0.63 | 46.5 | 67.7 | 0.61 |

TABLE 5

WWM and CMM Part 1 Study results without the armband inputs under one week of training, four days of validation, and 3 days of testing. The units for AD and AAD are mg/dL.

| | | | 7 Day Training | | | 4 Day Validation | | | 3 Day Testing | | |
|---|---|---|---|---|---|---|---|---|---|---|---|
| Subject | Method | Days | AD | AAD | $r_{fit}$ | AD | AAD | $r_{fit}$ | AD | AAD | $r_{fit}$ |
| 1 | WMM | 14.0 | 0.0 | 49.2 | 0.52 | 22.1 | 56.5 | 0.56 | 31.5 | 57.1 | 0.58 |
| 2 | WMM | 13.0 | 0.0 | 68.0 | 0.56 | −28.2 | 65.1 | 0.55 | 6.5 | 71.7 | 0.48 |
| 3 | WMM | 13.9 | 0.0 | 60.6 | 0.47 | 13.3 | 51.7 | 0.47 | 25.1 | 64.2 | 0.36 |
| 4 | WMM | 10.7 | 0.0 | 32.1 | 0.49 | 31.7 | 52.4 | 0.49 | 34.2 | 40.6 | 0.52 |
| 5 | WMM | 14.0 | 0.0 | 66.0 | 0.49 | 27.3 | 92.5 | 0.48 | −12.4 | 65.3 | 0.45 |
| 6 | WMM | 13.9 | 0.0 | 63.5 | 0.38 | 23.7 | 62.8 | 0.27 | −3.4 | 37.1 | 0.52 |
| 7 | WMM | 14.0 | 0.0 | 60.7 | 0.47 | 22.6 | 47.8 | 0.60 | −2.9 | 55.1 | 0.54 |
| 8 | WMM | 14.0 | 0.0 | 35.8 | 0.25 | 26.6 | 45.6 | 0.33 | −0.1 | 47.7 | 0.35 |
| 9 | WMM | 13.9 | 0.0 | 63.8 | 0.44 | −6.0 | 62.6 | 0.47 | −44.1 | 69.0 | 0.49 |
| 10 | WMM | 16.8 | 0.0 | 48.3 | 0.56 | 15.2 | 42.7 | 0.70 | 11.8 | 54.1 | 0.67 |
| 11 | WMM | 15.1 | 0.0 | 31.5 | 0.77 | −20.6 | 38.7 | 0.83 | −14.5 | 59.0 | 0.58 |
| Avg of Absolute Value | WMM | 13.9 | 0.0 | 52.7 | 0.49 | 21.6 | 56.2 | 0.52 | 17.0 | 56.4 | 0.50 |
| 1 | CMM | 14.0 | 37.5 | 65.2 | 0.63 | 53.4 | 78.8 | 0.54 | 83.8 | 105.3 | 0.64 |
| 2 | CMM | 13.0 | −3.6 | 65.7 | 0.69 | −70.6 | 88.4 | 0.65 | −48.1 | 70.2 | 0.70 |
| 3 | CMM | 13.9 | 0.9 | 60.3 | 0.44 | −8.9 | 53.4 | 0.53 | 0.0 | 59.7 | 0.18 |
| 4 | CMM | 10.7 | 0.7 | 30.2 | 0.62 | 58.3 | 64.6 | 0.52 | 64.6 | 65.3 | 0.47 |
| 5 | CMM | 14.0 | 0.4 | 63.3 | 0.57 | 6.5 | 87.8 | 0.39 | −85.3 | 97.9 | 0.49 |
| 6 | CMM | 13.9 | 0.8 | 58.0 | 0.53 | −9.8 | 56.5 | 0.61 | −11.3 | 37.4 | 0.55 |
| 7 | CMM | 14.0 | −0.1 | 55.5 | 0.57 | −16.6 | 49.9 | 0.54 | −69.9 | 77.7 | 0.75 |
| 8 | CMM | 14.0 | −1.2 | 35.9 | 0.36 | 17.1 | 42.4 | 0.36 | −13.9 | 51.6 | 0.35 |
| 9 | CMM | 13.9 | −0.1 | 61.5 | 0.45 | −21.5 | 63.9 | 0.46 | −103.7 | 118.9 | 0.47 |
| 10 | CMM | 16.8 | 0.7 | 47.4 | 0.60 | 20.5 | 42.6 | 0.75 | 27.4 | 58.1 | 0.60 |
| 11 | CMM | 15.1 | 0.1 | 32.1 | 0.73 | −46.6 | 53.8 | 0.80 | −1.0 | 56.4 | 0.58 |
| Avg of Absolute Value | CMM | 13.9 | 4.2 | 52.3 | 0.56 | 30.0 | 62.0 | 0.56 | 46.3 | 72.6 | 0.53 |

Tables 2-5 demonstrate that the performance goal for the CMM was an $r_{fit}$ similar to or better than the WMM. In addition, the present invention guarded well against overfitting as $r_{fit}$ values for Training and Validation are very similar. Table 2 contains results using all the inputs with one week of training and one week of validation. Table 3 represents the same conditions as Table 2 except for excluding the armband inputs. This shows that armband contributes significantly to in improving the fit; from an average $r_{fit}$ of 0.54 to 0.64 for the CMM. Tables 4 and 5 are for Subjects 1-11 with one week for Training, 4 days for Validation and 3 days for Testing. The averaged $r_{fit}$ values vary only slightly for the three data sets in both tables and for the WMM and the CMM. Again, the armband contributes significantly as the average $r_{fit}$ increases from 0.53 to 0.61. It is the inclusion of the additional activity variables as measured by the armband that create this desirable increase.

Using the equation for the WMM estimator for BGC, it can be determined that it is an inadequate structure in determining a dynamic food to insulin infusions relationship to achieve a targeted value of BC. This limitation is due to the separate additive nature of the equation for food consumption and insulin infusion, thus it is not capable of providing a food consumption/insulin infusion coupling relationship for BGC. This inadequacy was tested by setting all food inputs to zero with non-zero insulin infusion and vice versa. With all food inputs set to zero, under an assumption that BGC only changes for food consumption, $\hat{y}_t$ should drop to zero over time. In contrast, with insulin infusion set to zero, $\hat{y}_t$ should continue to increase over time.

Figure 6A:
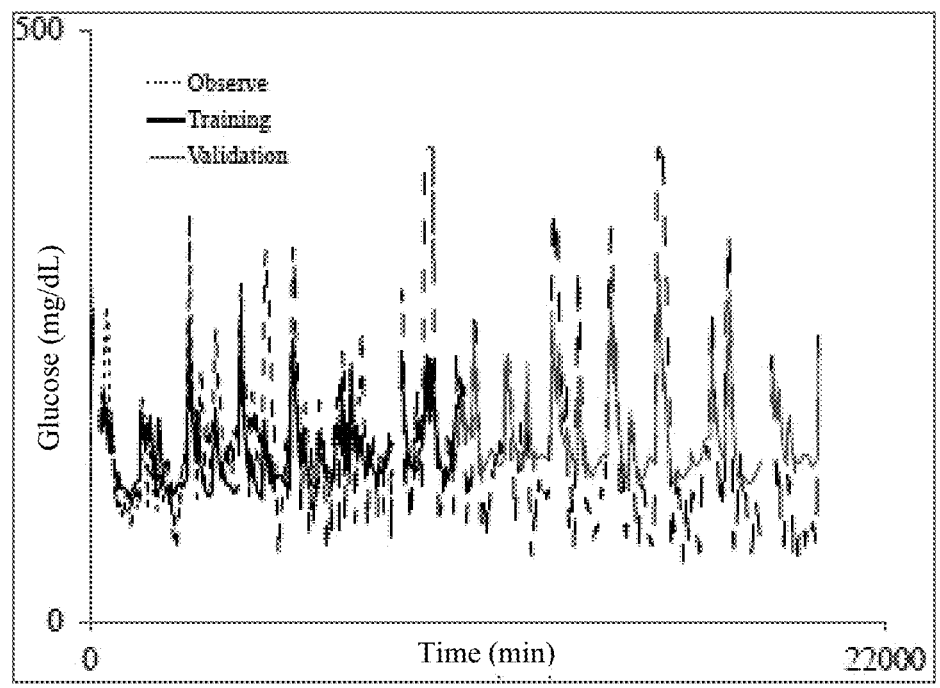
FIGS. 6A-C show the fitted response plots for Subject 11 with one week of training and one week of validation under a Wiener model method: (A) shows all inputs, (B) shows has no food consumption, and (C) has no insulin infusion.
Figure 6B:
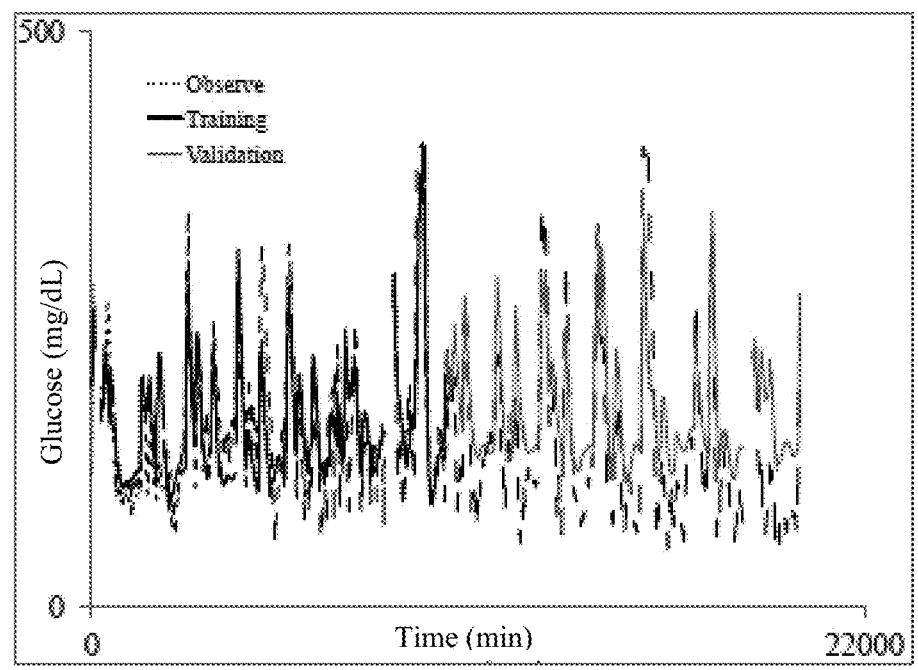
Figure 6C:
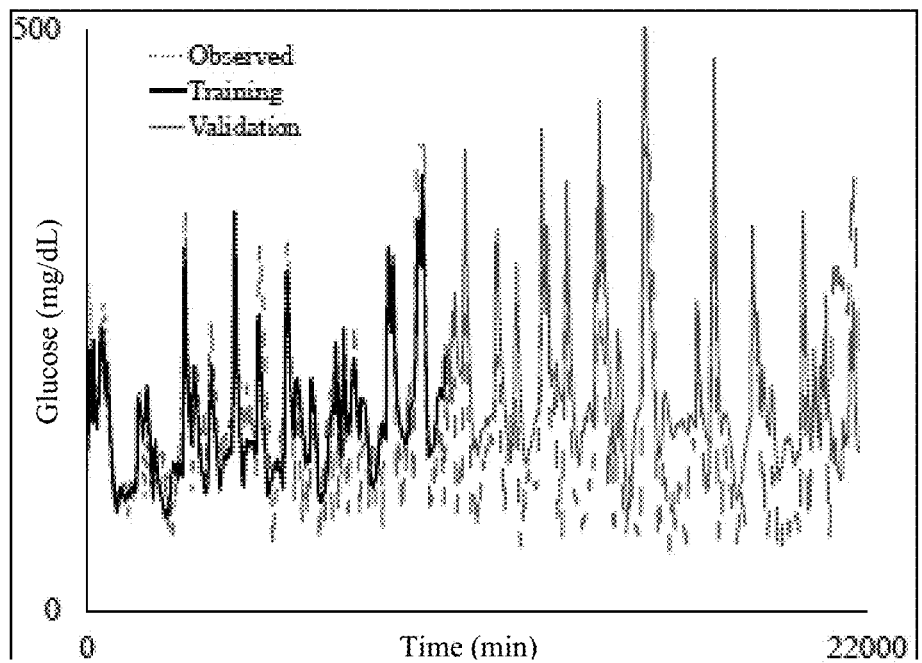

FIG. 6 illustrates this inadequacy on one of the fitted cases, Subject 11 with one week of training and one week of validation. FIG. 6a has all the inputs. FIG. 6b has no food consumption. FIG. 6c has no insulin infusion. FIG. 6a provides the fit with all the variables, and demonstrates the fit of the Validation data to the Training and Observation data is better than FIGS. 6b and 6c. Thus, the WMM structure is not adequate to give correct physiological coupled relationship between food intake and insulin infusion on BGC.

Figure 7A:
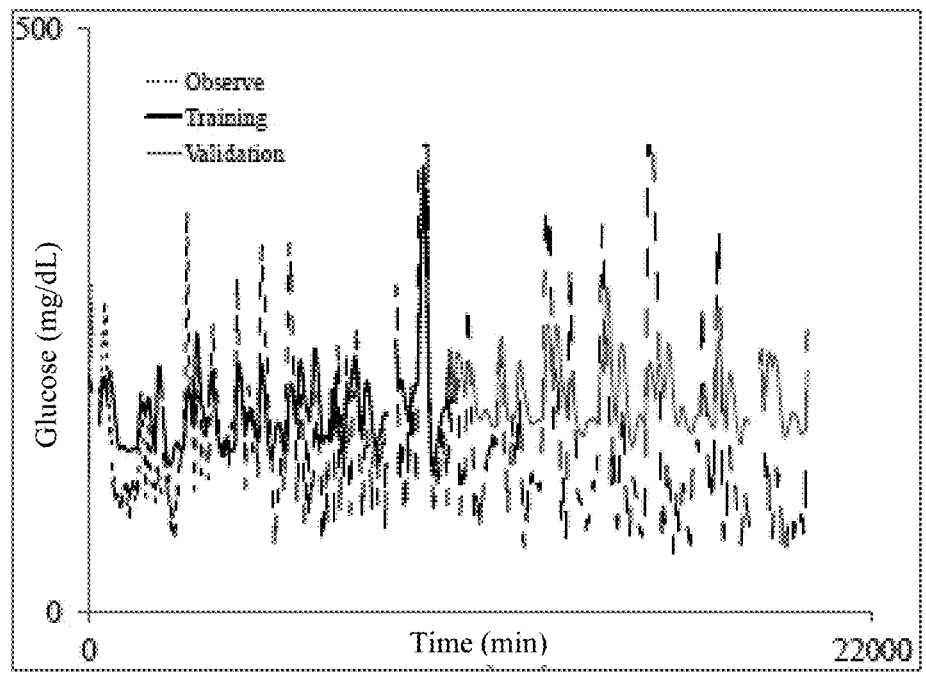
FIGS. 7A-C show the fitted response plots for Subject 11 with one week of training and one week of validation under an exemplary coupled model method of the invention: (A) shows all inputs, (B) shows has no food consumption, and (C) has no insulin infusion.
Figure 7B:
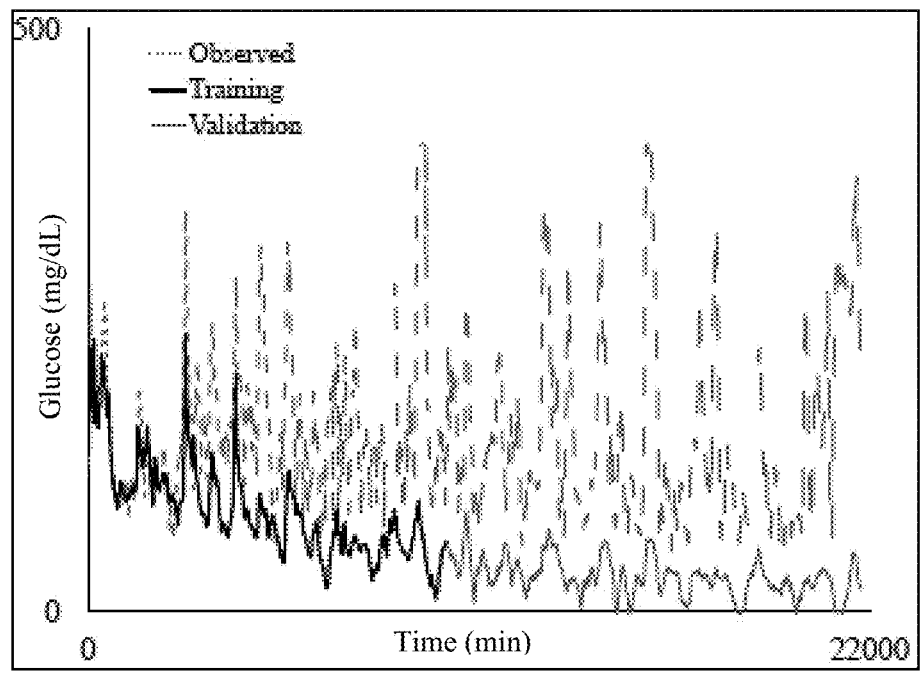
Figure 7C:
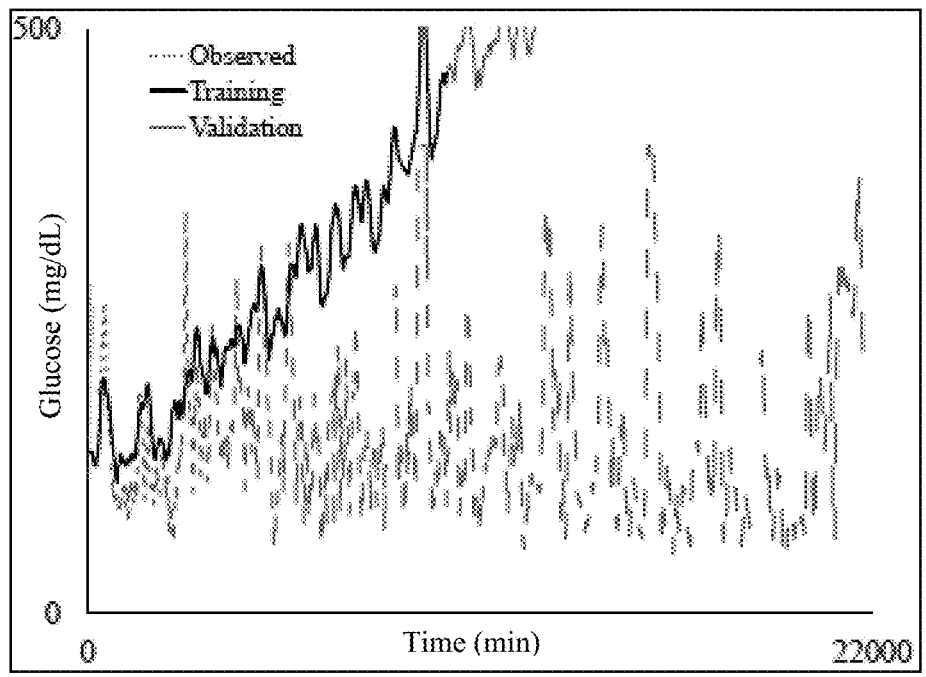

Results to evaluate the CMM for physiological soundness are shown in FIG. 7 for Subject 11 with one week of training and one week of validation. FIG. 7a provides the fit with all the variables included and the fit of Validation data to the Training and Observation data is still good. FIG. 7b depicts what occurs when all food coefficients in Equation 1 are set to zero. As shown, the fitted BGC drops steadily toward zero as it should. The response is oscillatory because, as seen by Equation 3, the activity variables are additive with respect to $V_{FI}$ and also contribute to BGC. Similarly, FIG. 7c depicts what occurs when the insulin infusion coefficient in Equation 2 is set to zero. The BGC rises steadily over time. Thus, not only does the CMM provide a good fit, but it also overcomes the WMM deficiencies in regards to zero insulin and food intake. Another critical advantage of CMM is the use of pseudo-BIC even though this output variable is unmeasured.

Example 2

Physiological soundness of CCM in its ability to provide realistic insulin infusion rates was evaluated by obtaining steady state relationships between carbohydrates ($x_c$), BGC ($y=V_{FI}=G$), insulin infusion rates ($x_I$). Using a backwards different finite derivative, in discrete form, Equation 1 becomes:

$$\frac{V_{FI,t} - V_{FI,t-\Delta t}}{\Delta t} = a_C v_{C,t} + a_F v_{F,t} + a_P v_{P,t} - a_{FI} I_t V_{FI,t} \tag{15}$$

And solving for $V_{FI,t}$ gives $$V_{FI,t} = \frac{(a_C v_{C,t} + a_F v_{F,t} + a_P v_{P,t})\Delta t + V_{FI,t-\Delta t}}{1 + a_{FI} I_t \Delta t} \tag{16}$$

Setting $a_0 = a_F = a_P = a_{A1} = \ldots = a_{Ap} = 0$, the previous equation becomes $$G_t = V_{FI,t} = \frac{a_C v_{C,t} \Delta t + G_{t-\Delta t}}{1 + a_{FI} I_t \Delta t} \tag{17}$$

At steady state, $V_{C,t} = X_{C,t} = X_C$, $V_{I,t} = X_{I,t} = X_I$, $G_t = G_{t-\Delta t} = \ldots = \overline{G}$, and
$I_t = I_{t-\Delta t} = \ldots = \overline{I}$, the previous equation becomes $$\overline{G} = \frac{a_C x_C \Delta t + \overline{G}}{1 + a_{FI} \overline{I} \Delta t} \tag{18}$$

Again by using a backwards difference finite derivative, in discrete, the previous equation becomes $$I_t = \frac{a_I v_{I,t} \Delta t + I_{t-\Delta t}}{1 + a_{BI} \Delta t} \tag{19}$$

At steady state, $V_{C,t} = X_{C,t} = X_C$, $V_{I,t} = X_{I,t} = X_I$, $G_t = G_{t-\Delta t} = \ldots = \overline{G}$, and $I_t = I_{t-\Delta t} = \ldots = \overline{I}$, and the previous equation becomes:

$$\overline{I} = \frac{a_I x_I \Delta t + \overline{I}}{1 + a_{BI} \Delta t} \tag{20}$$

And then simplifying from the previous equation $$\overline{I} = \frac{a_I}{a_{BI}} x_I \tag{21}$$

Combining the steady state equation for $\overline{G}$ and the previous equation and solving for $\overline{G}$ $$\overline{G} = \frac{a_C x_C \Delta t}{a_{FI} \overline{I} \Delta t} = \frac{a_C x_C}{a_{FI} \overline{I}} = \frac{a_C a_{BI} x_C}{a_{FI} a_I x_I} \tag{22}$$

And simplifying the previous equation by solving for $x_I$ $$x_I = \frac{a_C a_{BI}}{a_I a_{FI} \overline{G}} x_C \tag{23}$$

Figure 8:
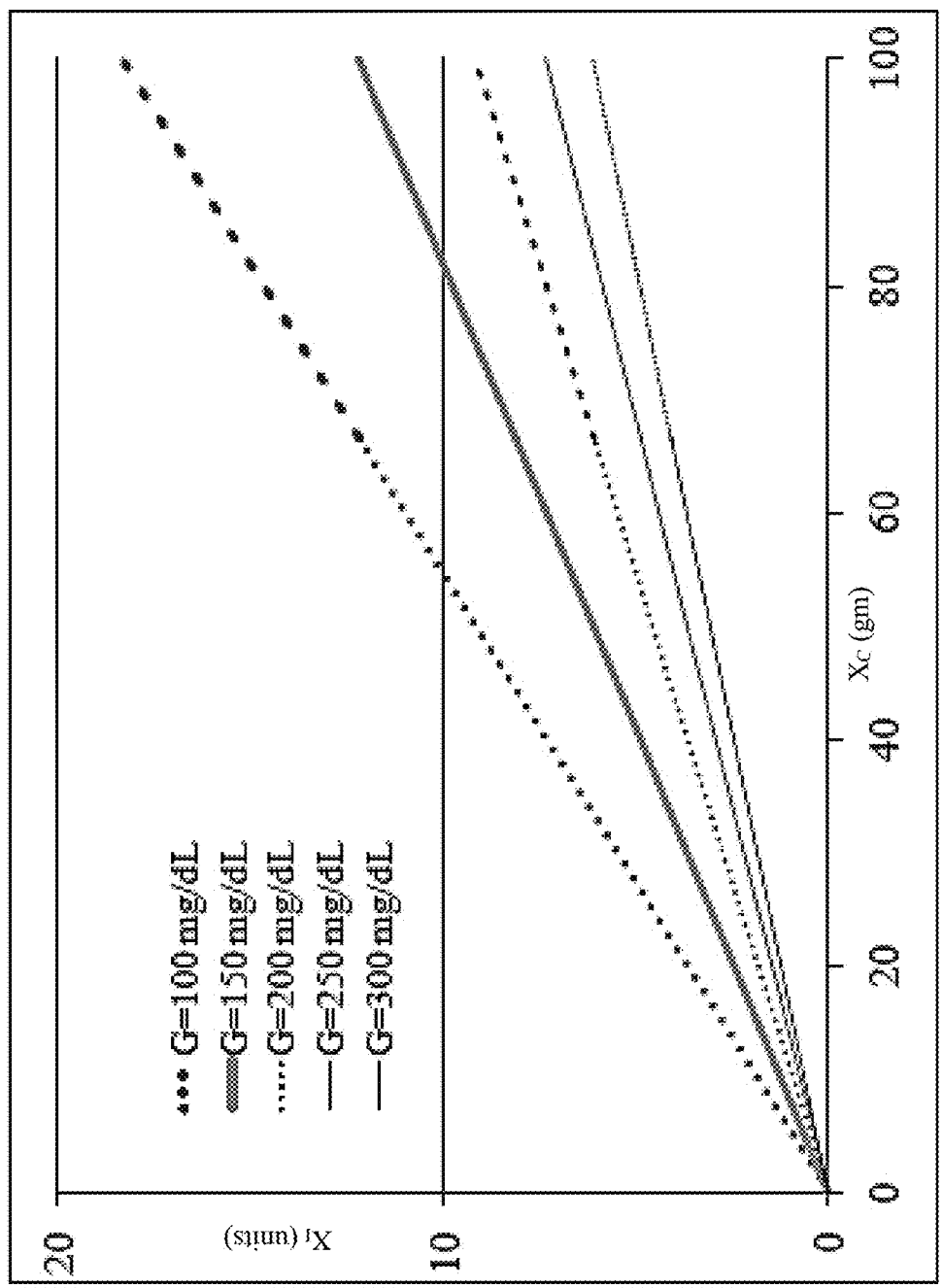
FIG. 8 is a graph showing the steady state relationship in the coupled modeling method of the invention for insulin and food consumption at constant BGC.

This final equation demonstrates the soundness of the model as $x_I$ is correctly proportional to $x_C$ while still being inversely proportional to $\overline{G}$. This relationship implies that for a constant consumption rate of carbohydrates, the insulin infusion rate to maintain a constant BGC level (i.e., $\bar{G}$), decreases as $\bar{G}$ increases. For example, a higher infusion rate is needed to maintain a BGC level of 100 mg/dL than to maintain a level of 300 mg/dL as additional insulin is required to decrease the level from 300 to 100 mg/dL. By substituting the estimated coefficients for a subject into Equation 23, an evaluation of this subject can be made on the basis of "realistic" results. This was done for Subject 11 and the results are plotted in FIG. 8, which shows the steady state relationship in the CCM for insulin infusion ($x_I$) and food consumption ($x_C$) at constant BGC (G).

As shown, at $x_C$=60 gm, $x_I$ ranges from 2.4 units to 7.3 units of insulin for $\bar{G}$ equal to 300 mg/dL to 100 mg/L, respectively. These values are very practical and thus, Equations 23 produces values that are quite realistic for this subject as they represent the range of values experienced by this subject during data collection. Note that when the model is actually implemented in a real control setting, the dynamic form will be manipulating insulin levels for some target value of BGC and thus, this ratio will vary dynamically based on a number of conditions at each time instant and specific to the subject's personal model. The analysis presented is a very practical check on the soundness of a modeling approach and, perhaps equally as important, on the soundness of a specific subject's model. Thus, an important contribution of this work is this practical evaluation and it is recommended for evaluation of feedforward control models.

Example 3

The application of the derived CCM FFC algorithm as previously discussed was illustrated using Subject 11 and its fit given in Table 4 using all the data. As shown by AAD (the average of the absolute difference between the measured and fitted BGC), model bias varies considerably between the data sets. The initial time, t=0, was selected the first night when the measured glucose was fairly stable and the subject was resting. At the selected time, $y_0=Y^{set}$=140 mg/dL. Thus $\hat{B}_0=\hat{y}_0-140$, where "^" is used to represent an estimate. For $B_t$, the algorithm of $\hat{B}_t = y_{t-\Delta t} - \hat{y}_{t-\Delta t}$ was used to estimate its value. With $y_{FFC,t}$ and $y_{NAC,t}$ as the observed BGC with FFC and the observed BGC with no automatic control, respectively, then $$y_{FFC,t} = y_{NAC,t} - (\hat{y}_t - \hat{y}_0) + \hat{B}_0 - \hat{B}_t \quad (24)$$
$$= y_{NAC,t} - (\hat{y}_t - \hat{y}_0) + (y_{NAC,0} - \hat{y}_0) - (y_{NAC,t-\Delta t} - \hat{y}_{t-\Delta t})$$

Note that $(\hat{y}_t - \hat{y}_0)$ is the amount that the model (i.e., the FF controller) "compensates" by insulin infusion when the bias is constant.

Figure 9A:
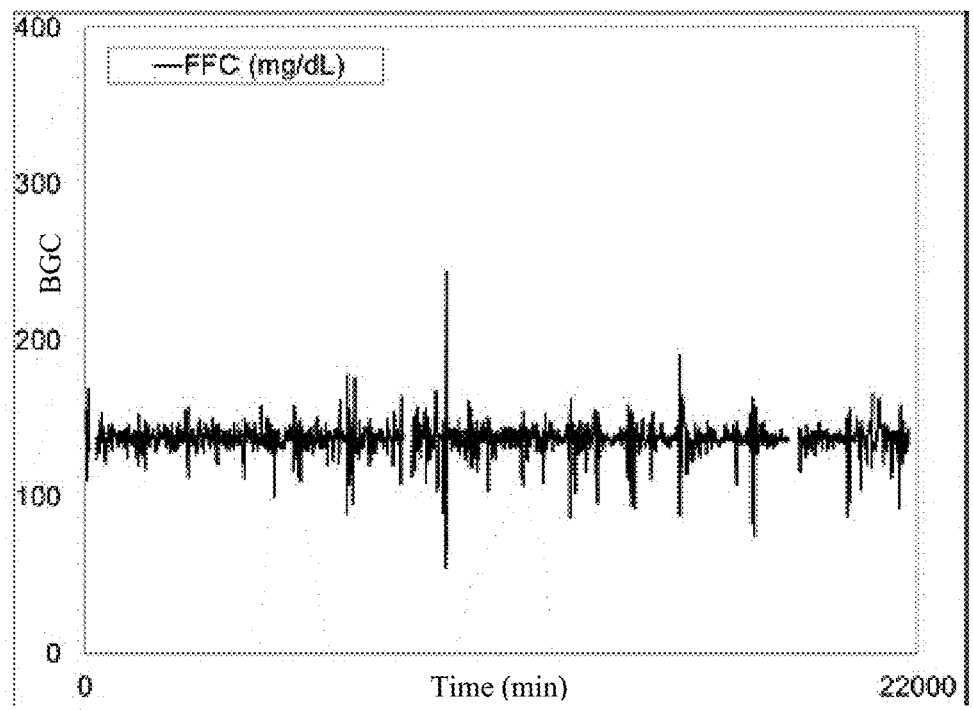
FIGS. 9A-B are graphs showing the potential reduction in BGC variability from use of the methods of the invention.
Figure 9B:
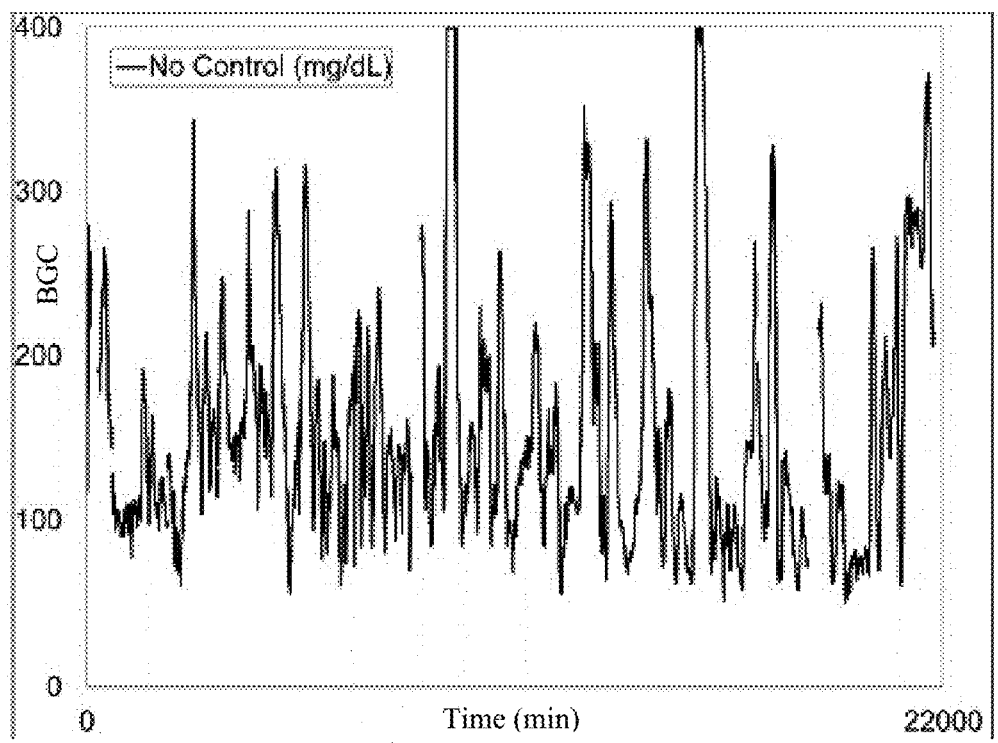

FIG. 9 shows the potential reduction in BGC variability from use of the proposed approach. FIG. 9a represents the two weeks of BGC data for Subject 11 and plots $y_{NAC,t}$ versus time in this analysis. FIG. 9b is $y_{FFC,t}$ versus time in this analysis for the fitted model in Table 4 for Subject 11. As shown, the variability is substantially reduced when comparing FIG. 9a without automatic control with FIG. 9b with the present invention. Thus, this level of the fitted model has the potential to greatly tightened BGC in an automatic FFC system. In this example, the variability is substantially reduced, with the standard deviations of $y_{NAC,t}(\sigma_{NAC})$ and $y_{FFC,t}(\sigma_{FFC})$ equal to 73.9 mg/dL and 8.7 mg/dL, respectively, that is a decrease of 88.3%.

Therefore, methods and systems have been described relating to insulin delivery. It should be understood that the present invention contemplates numerous variations, options, and alternatives. For example, where sensed information is provided as input, the sensed information may be supplied from any number of sensors including sensors associated with wearable devices, mobile devices, or other computing devices. Where information is input by users, it is to be understood that the information may be input using wearable devices, mobile devices, or other computing devices including the same device used for insulin delivery. It is further to be understood that the model may be stored on any number of computing devices including a mobile device, or the same device used for insulin delivery.

The above specification provides a description of the manufacture and use of the disclosed compositions and methods. Since many embodiments can be made without departing from the spirit and scope of the invention, the invention resides in the claims.

What is claimed is:

1. A method comprising steps of:
providing an insulin delivery system;
providing a feedforward model to determine an amount of insulin to administer, the model stored on a machine readable non-transitory media;
providing inputs to the model;
parameterizing the model using the inputs to provide an output;
administering insulin using the insulin delivery system based on the output, wherein the administration of insulin proactively nullifies the effect of any disturbances on blood glucose concentration.

2. The method of claim 1 wherein one or more of the inputs are provided by an automatic monitoring system.

3. The method of claim 2 wherein the automatic monitoring system comprises one or more sensors.

4. The method of claim 3 wherein the one or more sensors comprise at least one of the following a soft sensor, a remote sensor, an accelerometer, or a thermistor.

5. The method of claim 2 wherein the automatic monitoring system monitors at least one of the following variables body position, movement, heat dissipated, skin temperature, near body temperature, galvanic skin response, sleep, basal insulin, and bolus insulin.

6. The method of claim 1 wherein one or more of inputs are provided manually by a user.

7. The method of claim 6 wherein the one or more inputs provided manually by the user includes at least one of the following consumed energy, basal insulin, or bolus insulin.

8. The method of claim 1 further comprising computing the output from the model by executing instructions using a processor of the computing device.

9. The method of claim 1 wherein the insulin delivery system comprises an apparatus for administering insulin.

10. The method of claim 9 wherein the apparatus for administering insulin comprises a remotely controlled insulin pump.

11. The method of claim 1 wherein the model applies the feedforward control law $f_x(X_t;\hat{\theta})|_{x_{I,t}} - B_t - (f_x(X_0;\hat{\theta}) - B_0) = f_x(X_t;\hat{\theta})|_{x_{I,t}} - f_x(X_0;\hat{\theta}) + B_0 - B_t = 0$;
wherein $f_x(X_t;\hat{\theta})$ is a fitted function of input variables only, $X_t$ is a matrix of measured input variables, $\hat{\theta}$ is the vector of estimated parameters, and $B_t$ is the model bias at time t.

12. A system for administering insulin, the system comprising:

an insulin delivery system comprising an apparatus for administering insulin;
a plurality of sensors;
a feedforward model stored on a machine readable non-transitory media associated with a computing device, the computing device in operative communication with the plurality of sensors;
wherein the machine readable non-transitory media is capable of receiving one or more inputs and wherein the model parametrizes the one or more inputs to provide an output, wherein the output is computed by executing instructions by a processor of the computing device, wherein the computing device is in operable communication with the insulin delivery system.

13. The system of claim 12 further comprising a monitoring system, wherein the one or more inputs are provided by the monitoring system.

14. The system of claim 13 wherein the monitoring system monitors at least one of the following variables body position, movement, heat dissipated, skin temperature, near body temperature, galvanic skin response, and sleep, basal insulin, or bolus insulin.

15. The system of claim 12 wherein the one or more inputs are provided manually by a user.

16. The system of claim 15 wherein the one or more inputs provided manually by the user includes at least one of the following consumed energy, basal insulin, or bolus insulin.

17. The system of claim 12 wherein the plurality of sensors comprise at least one of the following a soft sensor, a remote sensor, an accelerometer, or a thermistor.

18. The system of claim 12 wherein the model applies the feedforward control law $f_x(X_t;\hat{\theta})|_{x_{I,t}} - B_t - (f_x(X_0;\hat{\theta}) - B_0) = f_x(X_t;\hat{\theta})|_{x_{I,t}} - f_x(X_0;\hat{\theta}) + B_0 - B_t = 0$;
wherein $f_x(X_t;\hat{\theta})$ is a fitted function of input variables only, $X_t$ is a matrix of measured input variables, $\hat{\theta}$ is the vector of estimated parameters, and $B_t$ is the model bias at time t.

19. An insulin delivery device, said device comprising:
an insulin pump;
an insulin monitoring device comprising one or more sensors; and
a feedforward model stored on a machine readable non-transitory media associated with a computing device, the computing device in operative communication with the one or more sensors;
wherein the machine readable non-transitory media is capable of receiving one or more inputs and wherein the model parametrizes the one or more inputs to provide an output, wherein the output is computed by executing instructions by a processor of the computing device, wherein the computing device is in operable communication with the insulin pump.

20. The device of claim 19, wherein the insulin pump is configured to administer a precise dosage of insulin based on the output of the model.

* * * * *